US00PP14454P29

(12) United States Plant Patent

Gerdts et al.

(10) Patent No.: US PP14,454 P2
(45) Date of Patent: Jan. 13, 2004

(54) PEACH TREE NAMED 'BURPEACHFIFTEEN'

(50) Latin Name: *Prunus persica*
Varietal Denomination: Burpeachfifteen

(75) Inventors: Timothy J. Gerdts, Kingsburg, CA (US); John K. Slaughter, Clovis, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 29 days.

(21) Appl. No.: 10/315,408

(22) Filed: Dec. 9, 2002

(51) Int. Cl.[7] ..... A01H 5/00
(52) U.S. Cl. ..... Plt./198
(58) Field of Search ..... Plt./198

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of peach tree (*Prunus persica*), and which is denominated varietally as 'Burpeachfifteen', and which further produces an attractively colored yellow-fleshed, freestone peach which is mature for harvesting and shipment approximately August 28 to September 8 under the ecological conditions prevailing in the San Joaquin Valley of Central California.

1 Drawing Sheet

BACKGROUND OF THE NEW VARIETY

The present invention relates to a new, novel and distinct variety of peach tree, *Prunus persica,* which has been denominated varietally as 'Burpeachfifteen'.

ORIGIN

The present variety of peach tree resulted from an on-going program of fruit and nut tree breeding. The purpose of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burpeachfifteen' was originated by us from a population of seedlings grown in our experimental orchards located near Fowler, Calif. The seedlings, grown on their own roots, were the result of a controlled cross of the yellow-fleshed 'B2.026' peach tree (unpatented) which was used as the seed parent and the white-fleshed, nectarine tree, 'B17.025', (unpatented) which was used as the pollen parent. One seedling, which is the present variety, exhibited especially desirable characteristics, and was designated as 'E24.018'. This seedling was marked for subsequent observation. After the 1999 season, the new present variety was selected for advanced evaluation and repropagation.

ASEXUAL REPRODUCTION

Asexual reproduction of the new and distinct variety of peach tree was accomplished by budding to 'Nemaguard' Rootstock (un-patented) after the 1999 growing season. This was performed by us in our experimental orchard located near Fowler, Calif. Subsequent evaluations performed in latter years have shown those asexual reproductions run true to the original tree. All characteristics of the original tree and its fruit were established and appear to be transmitted through succeeding asexual propagations.

SUMMARY OF THE VARIETY

'Burpeachfifteen' is a new and distinct variety of peach tree, which is of large size, and which has vigorous growth, and which further is a regular and productive bearer of relatively large, firm, yellow fleshed, freestone fruit having good flavor and eating quality. The tree has a medium chilling requirement of approximately 600 hours. The new tree also produces relatively uniformly sized fruit throughout the tree. The fruit further has a high degree of red skin coloration, and a firm flesh. The fruit also appears to have good handling and shipping qualities. Still further, the 'Burpeachfifteen' peach tree bears fruit which are ripe for commercial harvesting and shipment on approximately August 28 to September 8 under the ecological conditions prevailing in the San Joaquin Valley of Central California. In comparison to the peach tree variety, 'B2.026' which is the seed parent, the present variety, 'Burpeachfifteen' ripens at least about 12 or more days earlier.

BRIEF DESCRIPTION OF THE DRAWING

The accompanying drawing which is provided is a color photograph of the present variety. It depicts two whole mature fruit and one fruit is dissected substantially along the equatorial plane to expose the flesh and the pit thereof. Additionally a characteristic twig bearing typical leaves is shown. The external coloration of the fruit as shown is sufficiently matured for harvesting and shipment. The colors are as nearly true as is reasonably possible in a color representation of this type. Due to chemical development, processing and printing, the colors of the leaves and fruit depicted in these photographs may or may not be accurate when compared to the actual specimen. For this reason, future color references should be made to the color plates (Royal Horticultural Society) and the other descriptions provided for hereinafter.

DETAILED DESCRIPTION

Referring more specifically to the pomological details of this new and distinct variety of peach tree, the following has been observed in the fourth fruiting season under the ecological conditions prevailing at our orchard which is located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally. — Considered medium large when compared to other common commercial peach cultivars ripening in the early season of maturity. The tree of the present variety was pruned to a height of approximately 280.0 cm to 316.0 cm at maturity.

*Vigor.*—Moderately vigorous. The present variety grew from about 120.0 cm to 152.0 cm in height during the first growing season. The variety was pruned to a height of approximately 134.6 cm in the first dormant season and primary scaffolds were selected for the desired tree structure.

*Productivity.*—Productive. Fruit set varies from about twice to several times more than the desired crop load. Fruit set is spaced by thinning to develop the remaining fruit into the desired market size. Number of fruit set varies with climatic conditions and the cultural practices employed during the bloom period and is therefore not distinctive of the variety.

*Regularity of bearing.*—Regular. Fruit set has been observed as heavy and thinning was necessary during the past 4 years.

*Form.*—Upright, and pruned to a vase shape.

*Density.*—Medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements are approximately 650 hours below 7.0 degrees C. The variety appears to be hardy under typical Central San Joaquin Valley climatic conditions.

Trunk:

*Diameter.*—Approximately 17.1 cm in diameter when measured at a distance of approximately 15.24 cm above the soil level, at the end of the fourth growing season.

*Bark texture.*—Considered moderately rough, with numerous folds of papery scarfskin being present.

*Lenticels.*—Numerous flat, oval lenticels are present. The lenticels range in size from approximately 4.0 to 6.0 millimeters in width, and from 1.0 to 2.0 millimeters in height.

*Lenticel color.*—Considered an Orange Brown, (RHS Greyed-Orange Group N172 B).

*Bark coloration.*—Variable, but it is generally considered to be grey-brown, (RHS Greyed-Orange Group 175 A).

Branches:

*Size.*—Considered medium for the variety.

*Diameter.*—Average as compared to other varieties. The branches have a diameter of about 8.5 centimeters when measured during the fourth year after grafting.

*Surface texture.*—Average, and appearing furrowed on wood which is several years old.

*Crotch angles.*—Primary branches are considered variable and between about 42 to 53 degrees from the horizontal axis. This characteristic is not considered distinctive of the variety however.

*Current season shoots.*—Surface texture — Substantially glabrous.

*Internode length.*—Approximately 2.4 to 2.8 cm.

*Color of mature branches.*—Medium brown, (RHS Greyed-Orange Group 176 B).

*Current season shoots.*—Color. — Light green, (RHS Yellow Green Group 152 D). The color of new shoot tips is considered a bright and shiny green (RHS Green Group 141 B).

Leaves:

*Size.*—Considered medium large for the species. Leaf measurements have been taken from vigorous, upright, current-season growth at approximately mid-shoot.

*Leaf length.*—Approximately 150.0 to 164.0 millimeters.

*Leaf width.*—Approximately 33.0 to 47.0 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (approximately RHS Yellow-Green Group 146 A).

*Leaf texture.*—Glabrous.

*Lower surface.*—Medium green, (RHS Yellow-Green Group 146 C).

*Leaf venation.*—Pinnately veined.

*Mid-vein.*—Color. — Light yellow green, (RHS Yellow Green Group 145 A).

*Leaf margins.*—Slightly undulating. Form — Considered crenate, occasionally doubly crenate. Uniformity — Considered generally uniform.

*Leaf petioles.*—Size — Considered medium. Length — 9.0 to about 13.5 mm. Diameter — 1.5 to about 2.5 mm. Color — Medium green, (RHS Yellow-Green Group 146 C).

*Leaf glands.*—Size — About 1.0 mm in height and about 1.0 mm in width. Number — Generally one per side, occasionally two per side. Type — Globose, considered reasonably appressed to the petiole margin. Color — Orange brown, (RHS Grey-Brown Group199 B).

*Leaf stipules.*—Size — Considered medium large for the variety. Number — Typically 2 per leaf bud and up to 6 per shoot tip. Form — Lanceolate in form and having a serrated margin. Color — Green, (RHS Green Group 139 B) when young but graduating to a brown color, (RHS Greyed-Orange group N172 A) with advancing senescence. The stipules are considered to be early deciduous.

Flowers:

*Flower buds.*—Generally — The floral buds, depending upon the stage of development, are typically approximately 6.0 millimeters wide; about 12.0 millimeters long; conic in form; and slightly appressed relative to the bearing shoot.

*Flower buds.*—Color — The bud scales are reddish-brown, (approximately RHS Greyed Purple Group 183 A). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Mar. 3, 2000.

*Blooming time.*—Considered mid-season in comparison to other commercial peach cultivars grown in the central San Joaquin Valley. Date of full bloom was observed on Mar. 8, 2000. The date of bloom varies slightly with climatic conditions and cultural practices.

*Duration of bloom.*—Approximately 9 days. This varies slightly with climatic conditions.

*Flower type.*—The variety is considered to have a showy type flower.

*Flower size.*—Flower diameter at full bloom is approximately 38.0 to 42.0 millimeters.

*Bloom quantity.*—Considered abundant.

*Flower bud frequency.*—Normally 1 to 2 appear per node.

*Petal size.*—Generally — Considered medium for the species. Length — Approximately 16.0 to 20.0 millimeters. Width — Approximately 14.0 to 17.0 millimeters.

*Petal form.*—Broadly ovate.

*Petal count.*—Nearly always 5.

*Petal texture.*—Glabrous.

*Petal color.*—Light pink when young, (RHS Red Purple Group 65 B) and darkening with advancing senescence and exposure to sunlight to a medium to dark pink, (RHS Red Purple Group 65 A).

*Fragrance.*—Slight.

*Petal claw.*—Form — The claw is considered truncate, and has a medium-small size when compared to other varieties. Length — Approximately 6.0 to 8.0 millimeters. Width — Approximately 6.0 to 7.0 millimeters.

*Petal margins.*—Generally considered variable, from nearly smooth, to moderately undulate and ruffled, especially apically.

*Petal apex.*—Generally — The petal apices generally appear slightly grooved at the tip.

*Flower pedicel.*—Length — Considered medium-long, and having an average length of approximately 3.0 to 4.0 millimeters. Diameter — Considered average, approximately 2.0 millimeters. Color — A medium brown, (RHS Grey Brown Group N199 D).

*Floral nectaries.*—Color — A Dull orange red, (RHS Orange-Red Group 34 A).

*Calyx.*—Surface Texture — Generally glabrous. Color — A dull red, (approximately RHS Greyed Purple Group 183 A).

*Sepals.*—Surface texture — The surface has a short, fine pubescent texture. Size — Average, and ovate in form. Color — A dull red, (approximately RHS Greyed-Red Group 178 A).

*Anthers.*—Generally — Average to above average in length. Color — Red to reddish-orange dorsally, (approximately RHS Greyed Red Group 179 A).

*Pollen production.*—Pollen is abundant, and has a yellow color, (approximately RHS Yellow Orange Group 17 B).

*Filaments.*—Size — Variable in length, approximately 15.0 to 19.0 millimeters. Color — Considered white to a pinkish-white, (RHS Red Purple Group 62 D).

*Pistil.*—Number — Usually 1, rarely 2. Generally — Average in size. Length — Approximately 17.0 to 19.0 millimeters including the ovary. Color — Considered a very pale green, (approximately RHS Yellow Green Group 150 C). Surface Texture — The variety has a long pubescent pistil.

Fruit:

*Maturity when described.*—Firm ripe condition (shipping ripe). Date of first picking — Aug. 25, 2002. Date of last picking. — Sep. 8, 2002. The date of harvest varies slightly with climatic conditions.

*Size.*—Generally — Considered large, and uniform. Fruit size can be influenced by cultural practices.

*Average cheek diameter.*—Approximately 78.0 to 83.0 millimeters.

*Average axial diameter.*—Approximately 72.0 to 79.0 millimeters.

*Typical weight.*—Approximately 328.0 grams. This is highly dependent upon cultural practices and therefore not distinctive of the variety.

*Fruit form.*—Generally — Moderately oblate. The fruit is generally uniform in symmetry.

*Fruit suture.*—Shallow, and extending from the base to apex. No apparent callousing or stitching exists along the suture line.

*Suture.*—Color — This has a yellow to golden yellow background color, (approximately RHS Yellow-Orange Group 20 B) and occasionally having some additional red coloration, (approximately RHS Red Group 53 A).

*Ventral surface.*—Form — Slightly indented.

*Apex.*—Rounded.

*Base.*—Retuse.

*Stem cavity.*—Rounded to slightly elongated in the suture plane. Average depth of the stem cavity is about 1.45 cm. Average width is about 2.33 cm.

*Fruit skin.*—Thickness — Considered medium in thickness, and tenacious to the flesh. Texture — Short, fine pubescence. Taste — Non-astringent. Tendency to crack. — None observed.

*Color.*—Blush Color — This red blush color is variable from a reddish orange, (approximately RHS Orange-Red Group 33 B) to a dark red, (approximately RHS Red Group 53 A). Blush color ranges from about 75% to 90% of the fruit surface depending upon the sunlight exposure of the fruit and the prevailing growing conditions. Ground color — Yellow orange, (approximately RHS Yellow-Orange Group 20 B).

*Fruit stem.*—Medium in length, approximately 6.0 to 8.0 millimeters. Diameter — Approximately 2.0 to 3.0 millimeters. Color — Pale yellow-green, (approximately RHS Yellow-Green Group 144 C).

*Flesh.*—Ripens — Evenly. Texture — Firm, and dense. Considered non-melting. Fibers — A few, small, and tender ones are found. Aroma — Very slight. Eating quality — Very good. Flavor — Considered sweet and mildly acidic. The flavor is considered both pleasant and balanced. Juice — Moderate. Brix — About 14.5 degrees. This characteristic varies slightly with the number of fruit per tree, prevailing cultural practices, and the surrounding climatic conditions. Flesh Color — Pale yellow, (approximately RHS Yellow-Orange Group 15 C).

Stone:

*Type.*—Freestone.

*Size.*—Considered medium large for the variety.

*Length.*—Average, about 29.0 to about 32.0 millimeters.

*Width.*—Average, about 25.0 to about 27.0 millimeters.

*Diameter.*—Average, about 16.0 to 19.0 millimeters.

*Form.*—Obovoid.

*Base.*—The stone base is usually rounded, but may vary from rounded to straight.

*Apex.*—Shape. — The stone apex is raised and has an acute, short tip.

*Stone surface.*—Surface Texture — Irregularly furrowed toward the apex, and pitted toward the base. The stone exhibits substantial pitting laterally. Substantial grooving over the apical shoulders is also evident. Surface pitting is prominent generally, and more frequently, it is present basally. Ridges — The surface texture varies from sharp to rounded. Ventral Edge — Width — Considered medium, and having a dimension of approximately 3.7 to 5.7 millimeters when measured at mid-suture. The wings are most prominent over the suture line. Dorsal Edge — Shape. — Full, heavily grooved, and having jagged edges. The dorsal edge is moderately eroded over the apical shoulder.

*Stone color.*—The color of the dry stone is a medium-brown, (approximately Greyed-Orange Group RHS 166 C).

*Tendency to split.*—Splitting has not commonly been noted.

*Kernel.*—Size — Kernel is considered medium large. Form — Considered ovoid. Pellicle — Pubescence is not developed at fruit senescence. Color — (Approximately RHS Greyed-Orange Group 164 B).

*Use.*—The subject variety 'Burpeachfifteen' is considered to be a late maturing Peach tree which produces fruit that are considered firm, attractively colored, and which are useful for both local and long distance shipping.

*Keeping quality.*—Excellent. Fruit has stored well up to 21 days after harvest at about 1.0 degree Celsius.

*Shipping quality.*—Considered good. Fruit showed minimal bruising of flesh or skin damage after being subjected to normal harvesting and packing procedures.

*Resistance to insects and disease.*—No particular susceptibilities were noted. The present variety has not been tested to expose or detect any susceptibilities or resistances to any known plant and/or other fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree substantially as illustrated and described, and which is characterized principally as to novelty by producing an attractively colored yellow-fleshed, freestone peach which is mature for harvesting and shipment approximately August 28 to September 8 under the ecological conditions prevailing in the San Joaquin Valley of Central California.

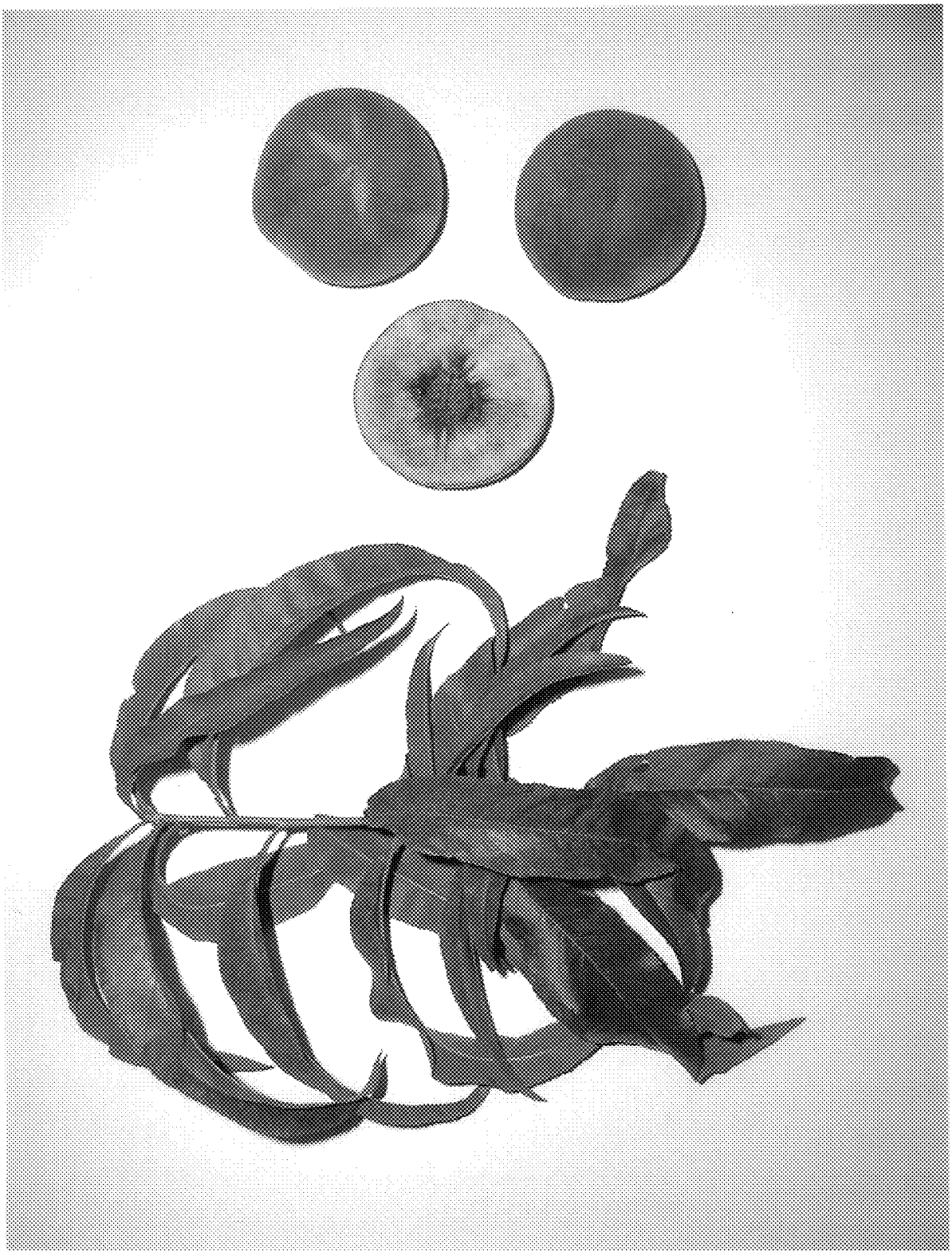

* * * * *